United States Patent [19]

Nakagawara et al.

[11] Patent Number: 6,014,583

[45] Date of Patent: Jan. 11, 2000

[54] HEMODYNAMICS MONITOR

[75] Inventors: Minoru Nakagawara, Tokyo; Ken-Ichi Yamakoshi, Ishikawa, both of Japan

[73] Assignee: NEC Corporation, Tokyo, Japan

[21] Appl. No.: 09/060,076

[22] Filed: Apr. 15, 1998

[30] Foreign Application Priority Data

Sep. 11, 1997 [JP] Japan .................................... 9-268151

[51] Int. Cl.⁷ ...................................................... A61B 5/05
[52] U.S. Cl. ............................................ 600/547; 600/506
[58] Field of Search .................................... 600/547, 382, 600/506, 522, 523, 536; 607/4, 98, 99, 148

[56] References Cited

U.S. PATENT DOCUMENTS

| | | |
|---|---|---|
| 4,437,469 | 3/1984 | Djordjevich et al. . |
| 4,562,843 | 1/1986 | Djordjevich et al. . |
| 4,617,939 | 10/1986 | Brown et al. . |
| 4,832,035 | 5/1989 | Cho et al. ............................ 128/633 |
| 4,905,705 | 3/1990 | Kizakevich et al. . |
| 5,103,828 | 4/1992 | Sramek . |
| 5,197,467 | 3/1993 | Steinhaus et al. . |
| 5,233,515 | 8/1993 | Cosman . |
| 5,311,878 | 5/1994 | Brown et al. . |
| 5,423,326 | 6/1995 | Wang et al. . |
| 5,443,073 | 8/1995 | Wang et al. . |
| 5,465,730 | 11/1995 | Zadehkoochak et al. . |
| 5,505,209 | 4/1996 | Reining . |
| 5,529,072 | 1/1996 | Sramek . |
| 5,634,467 | 6/1997 | Nevo . |
| 5,735,284 | 4/1998 | Tsoglin et al. . |
| 5,746,214 | 5/1998 | Brown et al. . |
| 5,749,369 | 5/1998 | Rabinovich et al. . |
| 5,782,763 | 7/1998 | Bianco et al. . |
| 5,807,251 | 9/1998 | Wang et al. . |
| 5,807,270 | 9/1998 | Williams . |

FOREIGN PATENT DOCUMENTS

| | | |
|---|---|---|
| 56-152602 | 11/1981 | Japan . |
| 63-206655 | 8/1988 | Japan . |

OTHER PUBLICATIONS

"BME" *Japanese Journal of Medical Electronic and Biological Engineering* vol. 35 Suppl. (Apr. 1997).

*Primary Examiner*—Marvin M. Lateef
*Assistant Examiner*—Shawne J Shaw
*Attorney, Agent, or Firm*—Foley & Lardner

[57] ABSTRACT

A constant current having high frequency and a known small current value is flown by a current supplying electrode portion (20) through a chest of a living body, variations of impedance at respective positions of the chest are detected by a voltage detector portion (30) and output as detected signals in relation to the respective positions of the chest and a mapping and display portion 40 performs a signal processing on the basis of the detected signals and produces a map corresponding thereto and displays it in a two dimensional plane. Therefore, it is possible to monitor hemodynamics in a wide area of the living body in two dimensional coordinates.

6 Claims, 6 Drawing Sheets

HEMODYNAMICS MONITOR

BACKGROUND OF THE INVENTION

The present invention claims priority from Japanese Patent Application No. 9-268151 filed Sep. 11, 1997, which is incorporated herein by reference.

1. Field of the Invention

The present invention relates to a hemodynamics monitor and, particularly, to a hemodynamics monitor for detecting and displaying a variation of impedance due to hemodynamics in a living body.

2. Description of Related Art

Figure 1:
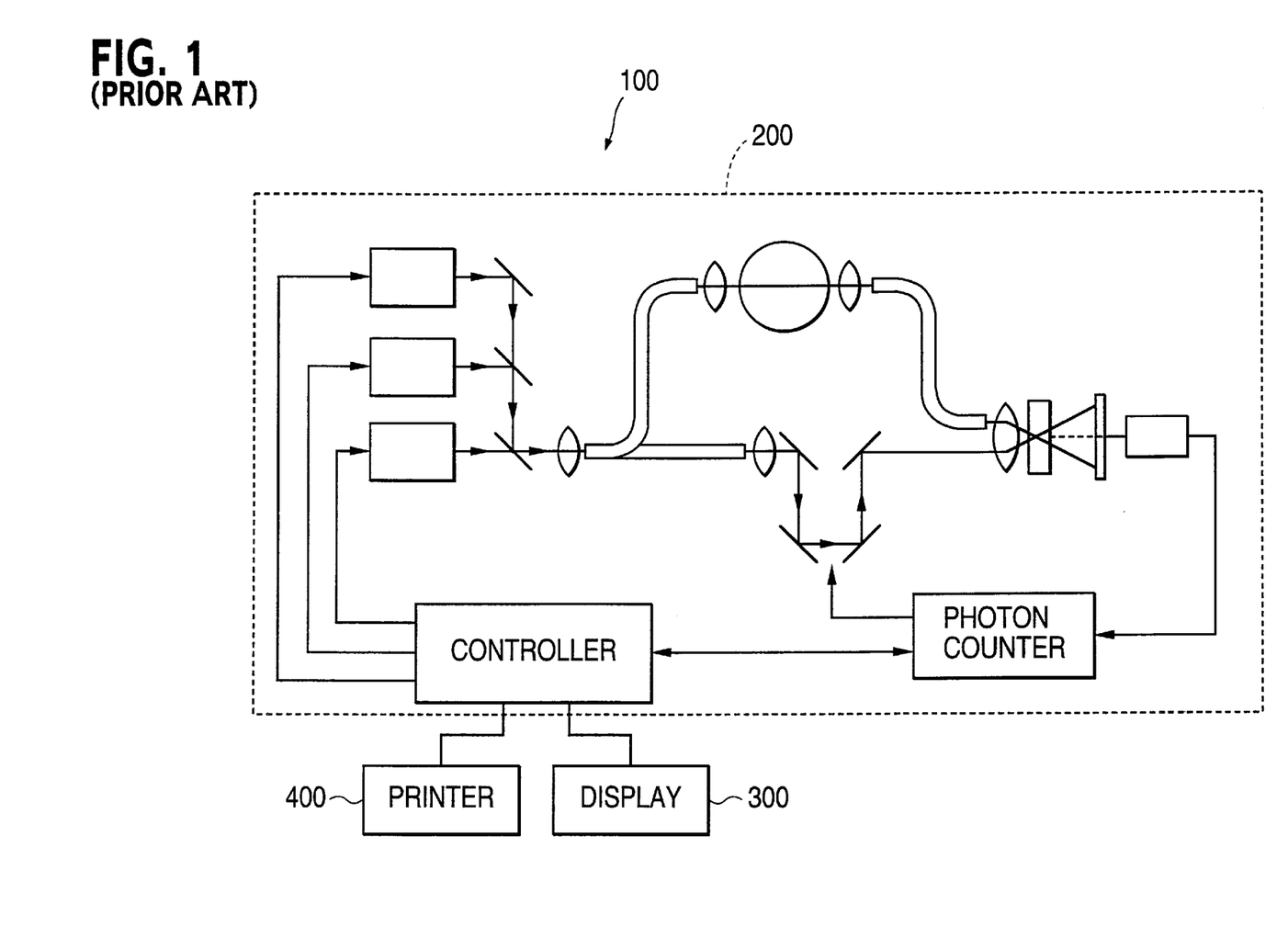
FIG. 1 is a block diagram showing a construction of a prior art hemodynamics monitor.

An example of a prior art hemodynamics monitor is disclosed in Japanese Patent Application Laid-open No. S63-206655. A construction of this hemodynamics monitor is shown in FIG. 1. In FIG. 1, the hemodynamics monitor 100 is provided with a measuring device 200 for measuring metabolic dynamics in a living body by utilizing a near infrared light passing through the living body along a predetermined axis thereof, a display 300 for displaying a result of measurement obtained by the measuring device 200 and a printer 400 for printing out the measurement result. With such construction of the hemodynamics monitor 100, the result of measurement obtained by measuring metabolic dynamics in the living body by utilizing the near infra red light passed through the living body along the predetermined axis thereof is monitored by the display 300 and printed by the printer 400.

Figure 2:
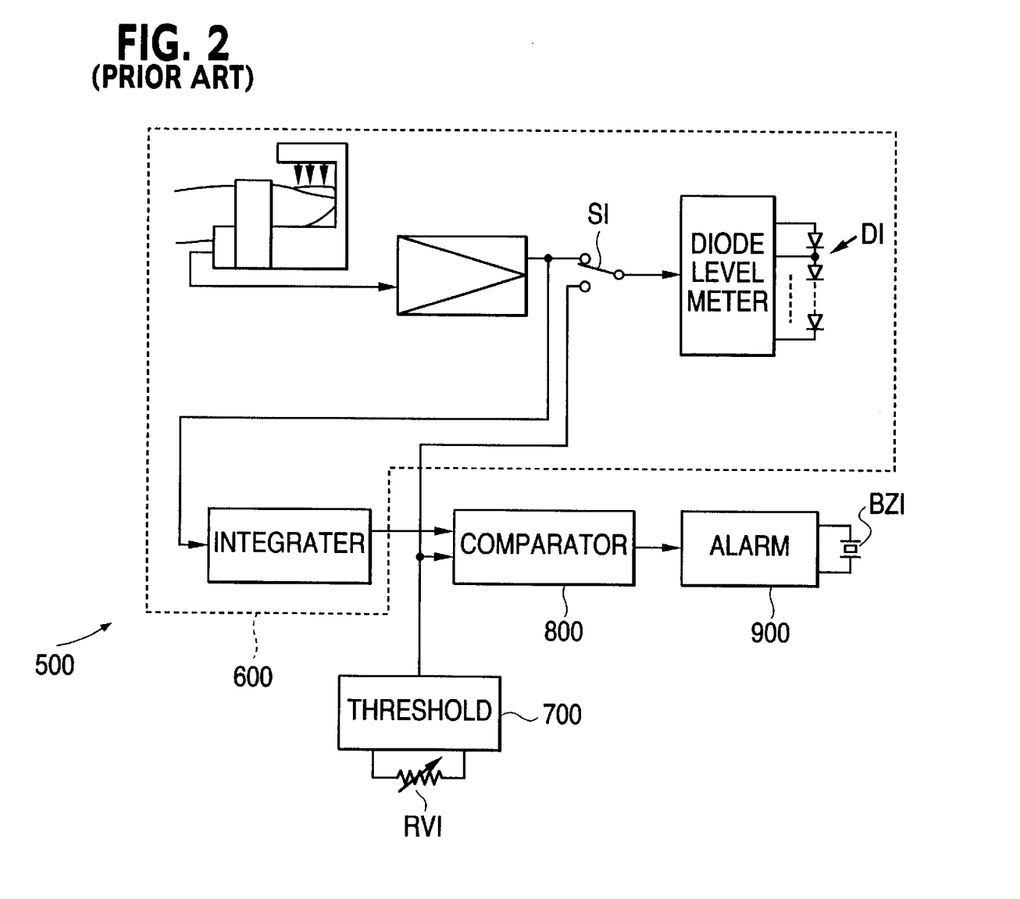
FIG. 2 is a block diagram showing a construction of another prior art hemodynamics monitor

Another example of the prior art hemodynamics monitor is disclosed in Japanese Utility Model Application Laid-open No. S56-152602. A construction of this example is shown in FIG. 2. In FIG. 2, the hemodynamics monitor 500 is provided with a finger type pulse wave detector 600 for sensing a sphygmic wave as an electric signal and generating an output corresponding to an average level of a plurality of pulse waves thus sensed, a threshold generator 700 for generating a threshold value corresponding to an abnormality of blood in peripheral artery due to thrombus, a comparator circuit 800 for comparing the output of the finger type pulse wave detector 600 with the threshold value and an alarm circuit 900 responsive to an output of the comparator circuit 800. The finger type pulse wave detector 600 senses pulse wave as the electric signal and generates the output corresponding to the average level for the plurality of the pulse waves and the comparator circuit 800 compares the output with the threshold value having a level corresponding to the abnormality of blood in peripheral artery due to thrombus. The alarm circuit 900 is activated in response to the output of the comparator circuit 800.

In each of the prior art hemodynamics monitors, only local hemodynamics on the predetermined axis of the living body or the finger is measured, so that, when the hemodynamics is monitored by the display 300 of the hemodynamics monitor 100, only local hemodynamics on the predetermined axis of the living body or the finger can be monitored.

SUMMARY OF THE INVENTION

An object of the present invention is to provide a hemodynamics monitor which measures hemodynamics in a wide area of a living body and monitors it in a two dimensional coordinates.

In order to achieve the above object, a hemodynamics monitor according to the present invention is featured by comprising a pair of electrodes for flowing a predetermined electric current through a portion of a living body, a detector means for detecting variations of impedance at a plurality of detection points of the portion of the living body which are located between the electrodes and providing an output corresponding to the result of detection obtained at the detection points in relation to the location of the detection points and a display means for displaying the output of the detector means in two dimensional coordinates.

That is, the variations of impedance at the plurality of detection points located in the living body are detected by flowing the predetermined current through the portion of the living body between the paired electrodes and the impedance variations are output in relation to the location of the detection points, which is displayed in two dimensional coordinates.

The electrodes may be any provided that they can flow the predetermined electric current through the portion of the living body, and may be of a type which can be attached to a chest or limbs of the living body.

The detector means may also be any, provided that it can detect differences between a reference impedance and impedances detected at the detection points located between the electrodes.

The reference impedance for detecting the variations of impedances at the detection points by the detector means may be an impedance immediately before the blood driving cycle of heart. That is, the detector means may detect the variations of the impedances at the respective detection points with respect to the impedance immediately before the blood driving cycle of the heart as the reference impedance.

Alternatively, the detector means may be constructed to detect variations of impedance at the respective detection points with respect to an impedance in a predetermined phase of a cardiac cycle as the reference. That is, the detector means may detect the variations of the impedances at the respective detection points with respect to the impedance in the predetermined phase of the cardiac cycle as the reference impedance. The display means which may include a display device and/or a printer may be any, provided that it can display the result of detection from the detector means in two dimensional coordinates.

The display means may be constructed such that it displays the output of the detector means in time series. That is, the display means displays the detection result output from the detector means in time series. Such time series display of the detection result is advantageous in that it is possible to confirm the variation of impedance with time. However, the display means is not limited to thereto and, in view of the intended display means, the latter can be constructed to display the detection result at only a desired time instance.

The present invention is not to be embodied by a specific apparatus and can be embodied by a combination of existing devices. Alternatively, the present invention can be embodied as a software for controlling these devices. Such software may be commercially available in the form of a recording medium such as magnetic recording medium or optical recording medium. Further, the software is not always required to realize the whole of the above mentioned function of the hemodynamics monitor. That is, it is possible to realize a portion of the function by a hardware and the remaining portion by a software. Alternatively, it is possible to record a software of a portion of the function on a recording medium and adaptively read it on demand.

BRIEF DESCRIPTION OF THE DRAWINGS

Embodiments of the present invention will be described in detail with reference to the accompanying drawings, wherein.

DETAILED DESCRIPTION OF THE PREFERRED EMBODIMENTS

Figure 3:
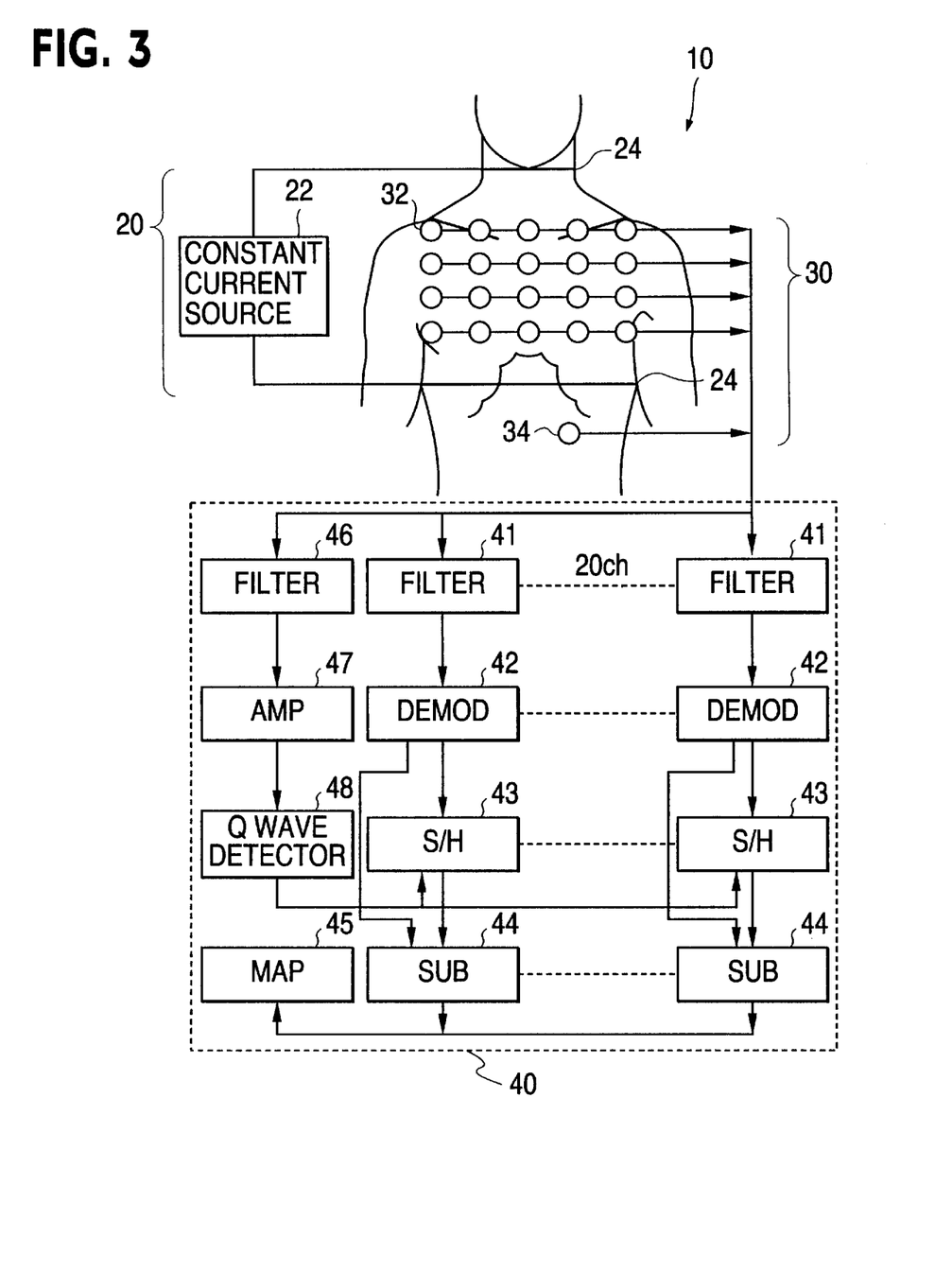
FIG. 3 is a block diagram showing a construction of a hemodynamics monitor according to an embodiment of the present invention.

FIG. 3 is a block diagram of an embodiment of the present invention. In FIG. 3, a hemodynamics monitor 10 is provided with an electrode portion 20 for flowing a known constant small current of high frequency through a chest portion of a living body, a voltage detector portion 30 for detecting variations of voltage at respective portions of the chest portion and supplying an output of the detected variations of voltage in relation to positions of the respective portions and a mapping and display portion 40 for processing the output, producing a map corresponding thereto and displaying the map.

The electrode portion 20 is constructed with a constant current source 22 for supplying a constant high frequency current having a small current value and a pair of electrodes 24 which are connected to the constant current source 22 and can be attached to a neck portion of the living body and a lower portion of the chest portion of the living body, respectively. A user attaches the electrodes 24 to the neck portion and the lower portion of the chest portion of the living body, respectively, and supplies the constant current having high frequency and the known small current value through the neck portion to the lower portion of the chest portion of the living body, or vise versa.

The voltage detector portion 30 is constructed with a voltage detection matrix 32 including a plurality, for example, 20, of detection electrodes which can be attached to the chest portion, detecting variations of voltage at the respective detection electrodes and supplying a result of detection in relation to positions of the detection electrodes and an electrode 34 which is used as a reference electrode for detecting the variations of voltage at the respective detection electrodes. The user attaches the detection electrodes to the chest of the living body and the voltage detector portion 30 detects the variations of voltage at the respective detection electrodes and outputs the result of detection in relation to the positions of the detection electrodes as a detected signal. Although, in this embodiment, the detection electrodes are attached to the chest portion, the positions of the detection electrodes may be any, provided that the positions are in a portion of the living body, and the positions may be in limbs of the living body. Further, the number of detection electrodes may be any.

The mapping and display portion 40 is constructed with filters 41 each for passing only a constant current component of the detected signal output from the voltage detector portion 30, demodulators 42 each for converting the signal component passed through the filter 41 into a D.C. current and supplying voltage signals Zn (n is a channel number and n=1, 2, . . . ), sample-hold circuits 43 each for holding the output voltage signal and supplying it at a predetermined timing, subtracters 44 each for subtracting the voltage signal output from the sample-hold circuit 43 as a subtrahend from the voltage signal output from the demodulator 42 as a minuend and supplying a difference therebetween as a subtraction result signal and a mapping and display device 45 for producing a map on the basis of the subtraction result signals and displaying it.

Among the 20 detection electrodes of the voltage detector portion 30, those in suitable positions output electrocardiogram (ECG) signals. In order to process these electrocardiogram signals, the mapping and displaying portion 40 further comprises an electrocardiogram filter 46 for passing only the electrocardiogram signals, an electrocardiogram amplifier 47 for amplifying the electrocardiogram signals passed through the electrocardiogram filter 46 and a Q wave detector 48 for generating a pulse (T) synchronized with a Q wave of the electrocardiogram signal.

Figure 4:
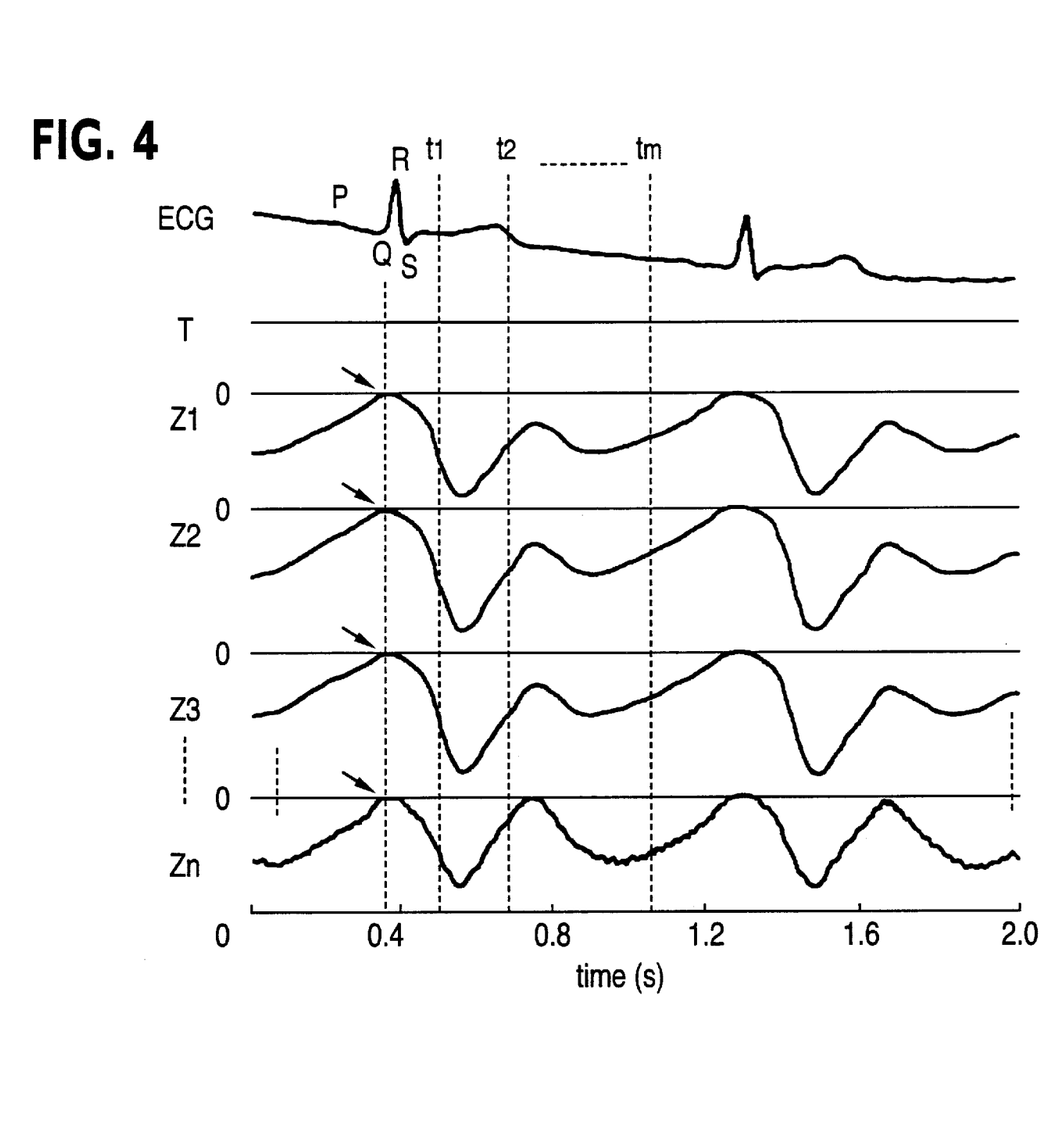
FIG. 4 shows waveforms of respective signals contained in a detected signal, showing variations of the respective signals with time.

With this construction of the hemodynamics monitor, the detected signals obtained at the voltage detector portion 30 are supplied to the filters 41 to pass only the signal component from the constant current source. The demodulators 42 convert these signal components such as shown in FIG. 4 into the D.C. voltages and supply the voltage signals proportional to the impedances at the respective detection electrodes to the sample-hold circuit 43.

On the other hand, the electrocardiogram signals output from the voltage detector portion 30 are supplied to the electrocardiogram filters 46 and the electrocardiogram signals passed through the electrocardiogram filters 46 are amplified by the electrocardiogram amplifiers 47, respectively. In response to the amplified electrocardiogram signals, the Q wave detector 48 generates the pulses synchronized with the Q waves of the electrocardiogram signals and supplies them to the sample-hold circuits 43. The sample-hold circuits 43 always sample the voltage signals from the demodulators 42 and, in response to the pulses from the Q wave detector 48, hold the voltage signals (sample signals) sampled with the timing of the pulses.

The subtracters 44 subtract the voltage signals (hold signal) held by the sample-hold circuits 43 from the voltage signals from the demodulators 42, respectively, and output the differences between them. The mapping and display device 45 produces the two dimensional map of the impedance variations at the respective detection electrodes corresponding to the hemodynamics in the living body, according to the differences and the known coordinates of the respective detection electrodes and displays it.

Figure 5:
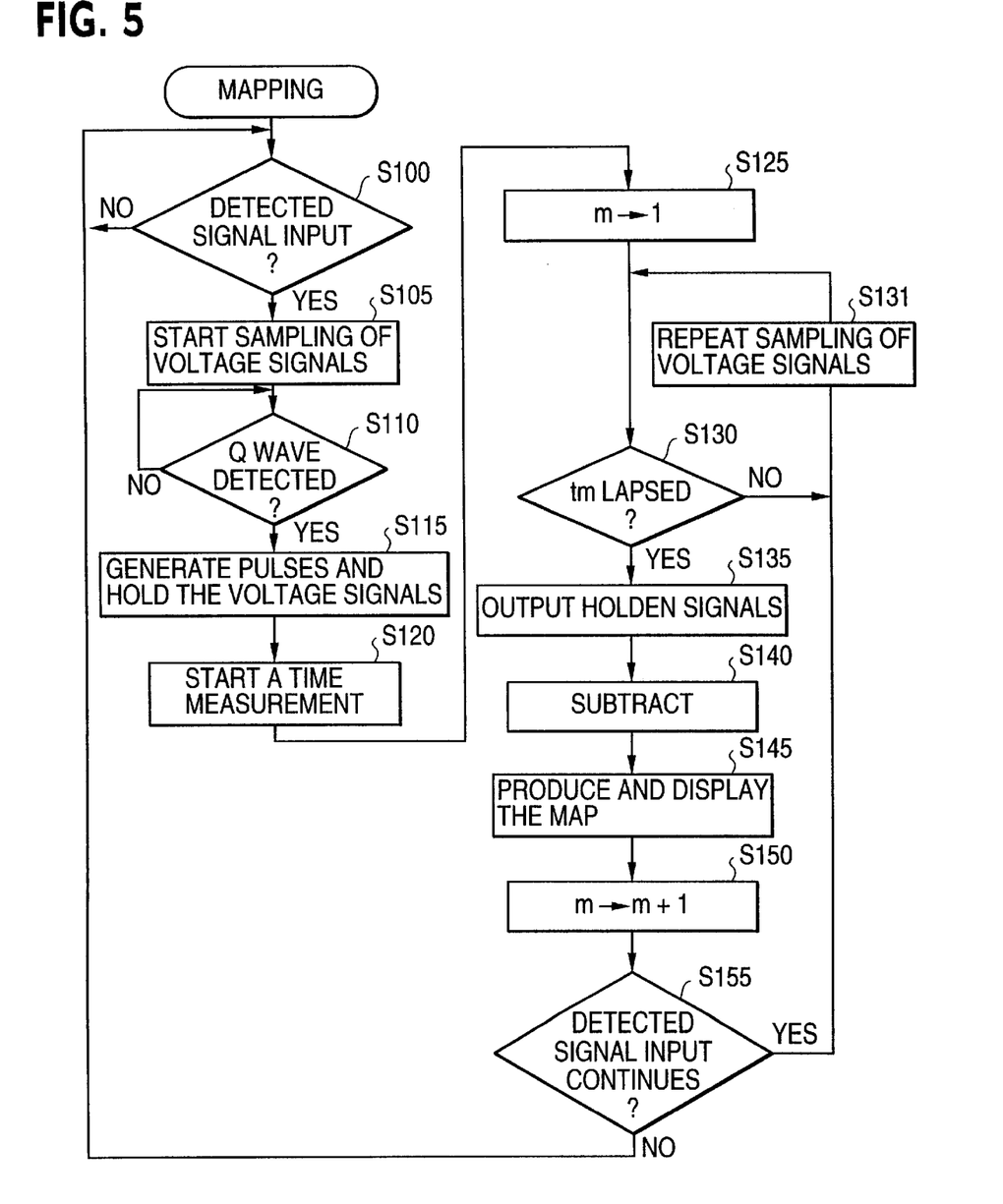
FIG. 5 is a flowchart showing procedures of a mapping operation.
Figure 6A:
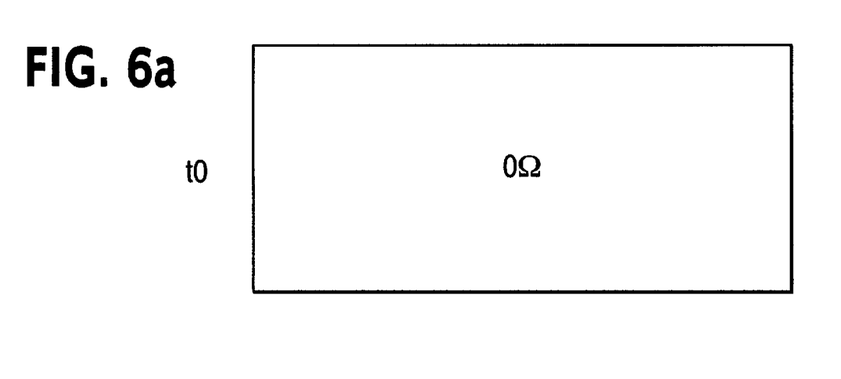
FIG. 6a to FIG. 6d are maps showing variations of impedance at respective detection electrodes with time.
Figure 6B:
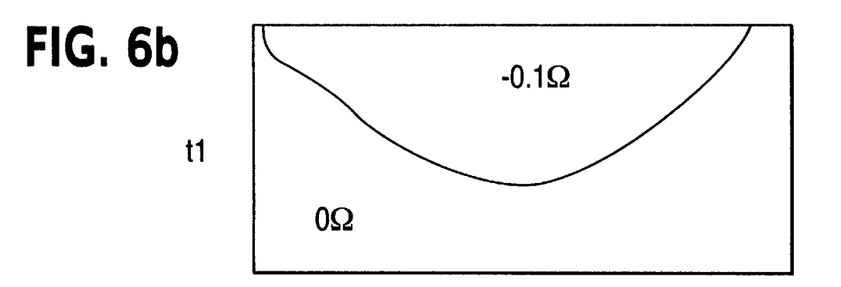
Figure 6C:
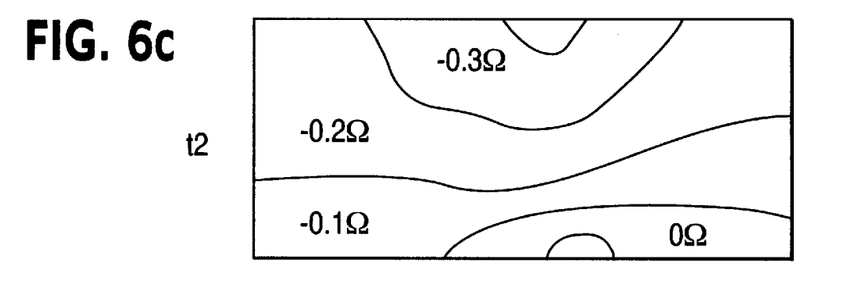
Figure 6D:
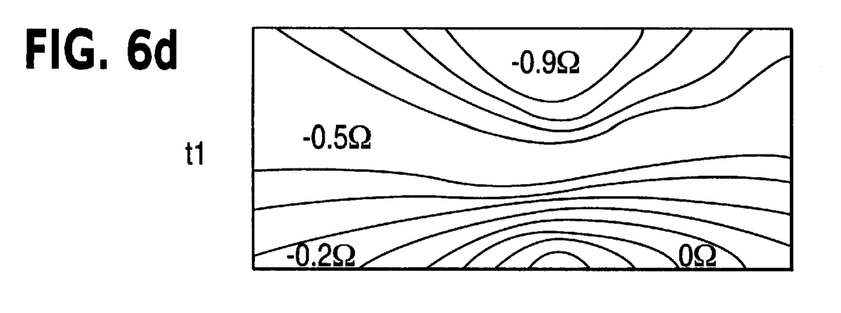

An operation of the hemodynamics monitor from a time at which the detected signal is input to the mapping and display device 40 to a time at which the map produced on the basis of the detected signals is displayed will be described with reference to FIG. 5.

When the detected signals are input to the mapping and display device 40 (step S100), the respective sample-hold circuits 43 start to sample the detected signals (step S105). When the Q wave detector 48 detects the Q waves (step S110) and generates the pulses, the respective sample-hold circuits 43 hold the respective sampled voltage signals (step S115). And, a time measurement is started (step S120) and the value of m is made (step S125), and the operation is in an idle state until the time t1 lapses (steps S130 and S131), while repeating the sampling operation. When the time t1 lapses, the respective sample-hold circuits 43 output the holden signals (step S135).

Then, the respective subtracters 44 subtract the sample signals from the demodulators 42 input to the minuend inputs thereof from the hold signals input to the subtrahend inputs thereof and output the differences as the subtraction result signals (step S140) and the mapping and display device 45 produces the map on the basis of the subtraction result signals and displays it (step S145). Then, the Q wave detector 48 adds 1 to m, resulting in m=2 (step S150) and becomes in an idle state until a time t2 lapses, while confirming that the detected signals are continuously input (steps S155 and S130).

In this manner, the mapping and display device 40 produces the map by repeating the hold of the detected signals and the output of the held detected signals until the input of detected signal is stopped and continuously display the variation of hemodynamics in time series as shown in FIG. 6*a* to FIG. 6*d*.

Although the mapping and display device 40 realizes the above operation by a combination of hard logics, the mapping and display device 40 is not always constructed in this manner. For example, it is possible to provide a micro processor (MPU) in the mapping and display device 40, to activate a mapping process program written in an ROM connected to the MPU and to execute the above mentioned mapping operation.

Further, although the mapping and display device 40 is provided with the samplehold circuits 43 and the subtracters 44, it is enough to extract the voltage signals based on the detected signals obtained from the respective detection electrodes when a predetermined time lapses from the pulses. Therefore, it is possible to realize such function by using voltage clamp circuits and/or a combination of A/D converters and digital arithmetic operations.

Further, although the present hemodynamics monitor uses the time at which the Q wave appears as the reference, it is enough to detect the variation of the detected signal with time on the basis of a predetermined reference and, therefore, cardiac sound or pulse wave or other time phase or an event of injection of medication may be used as the reference.

As described hereinbefore, since, in the present invention, a constant current having high frequency and a known small current value is flown by a current supplying electrode portion 20 through a chest of a living body, variations of impedance at respective positions of the chest are detected by a voltage detector portion and output as detected signals in relation to the respective positions of the chest and a mapping and display portion 40 performs a signal processing on the basis of the detected signals and produces a map corresponding thereto and displays it in a two dimensional plane. Therefore, it is possible to monitor hemodynamics in a wide area of the living body in two dimensional coordinates.

What is claimed is:

1. A computer program product comprising a computer useable medium having computer program logic recorded thereon for enabling a processor in a computer system to monitor hemodynamics of a living body, said computer program logic comprising:

means for enabling the processor to flow a predetermined current through a portion of the living body between a pair of electrodes;

means for enabling the processor to detect variations of impedance at a plurality of detection points arranged between said electrodes;

means for enabling the processor to output detected signals obtained at the detection points in relation to positions of the detection points;

means for enabling the processor to provide a voltage detection;

means for enabling the processor to map a two dimensional map of said impedance variations at the respective detection points, including sampling said detected signals, detecting the Q wave portion of said detected signals, and generating a pulse corresponding to said Q wave portion; and means for enabling the processor to display said two dimensional map.

2. A hemodynamics monitor comprising:

a pair of electrodes for flowing a predetermined current through a portion of a living body;

a detector for detecting variations of impedance at a plurality of detection points arranged between said electrodes and outputting detected signals obtained at the detection points in relation to positions of each of the detection points, said detector including a voltage detection matrix that includes a plurality of detection electrodes corresponding to the plurality of detection points and a reference electrode for detecting variations of voltage at the respective detection points, said detected signals of said detector being proportional to an impedance at a respective detection point;

a filter for filtering out detection signal components from said detected signals of said detector;

a demodulator for converting said detection signal components into output voltage signals;

sample and hold circuitry for holding said output voltage signals to generate respective holden signals and supplying said holden signals at a predetermined timing; and a subtractor for subtracting said respective holden signals from a predetermined portion of said respective output voltage signals from said demodulator to produce subtraction result signals;

a signal coupler coupling said predetermined portion of said voltage signals to said subtractor;

a mapping processor for producing a two dimensional map based on said subtraction result signals, said two dimensional map representative of impedance variations at the respective detection points; and a display for displaying said subtraction result signals in two dimensional coordinates.

3. The hemodynamics monitor of claim 2, further comprising:

an electrocardiogram filter for passing only electrocardiogram signals;

an amplifier for amplifying said filtered electrocardiogram signals; and a Q wave detector for generating a pulse synchronized with a Q wave portion of said electrocardiogram signal.

4. A hemodynamics display method comprising the steps of:

flowing a predetermined current through a portion of a living body between a pair of electrodes;

providing a voltage detection matrix that includes a plurality of detection electrodes corresponding to the plurality of detection points and a reference electrode for detecting variations of voltage at the respective detection points, said detected signals being proportional to impedances at the respective detection points;

detecting variations of impedance at a plurality of detection points arranged between said electrodes;

outputting detected signals obtained at the detection points in relation to positions of the detection points;

producing a two dimensional map of said impedance variations at the respective detection points, including sampling said detected signals, detecting the Q wave portion of said detected signals, and generating a pulse corresponding to said Q wave portion; and displaying said two dimensional map.

5. The hemodynamics display method of claim 4, wherein said producing step further comprises:

holding said sampled detected signals;

beginning a time measurement such that after a first predetermined time a plurality of holden signals are outputted;

subtracting said sampled detected signals from respective holden signals to produce subtraction result signals;

outputting said subtraction result signals; and producing said two dimensional map on the basis of said subtraction result signals.

6. The hemodynamics display method of claim 4, further comprising:

generating a time series display of two dimensional maps.

* * * * *